US00PP33893P2

(12) United States Plant Patent
Randag

(10) Patent No.: US PP33,893 P2
(45) Date of Patent: Jan. 18, 2022

(54) CALLA LILY PLANT NAMED 'DOZANATLA'

(50) Latin Name: *Zantedeschia sprengeri*
Varietal Denomination: Dozanatla

(71) Applicant: Dümmen Group B.V., De Lier (NL)

(72) Inventor: Cecilius Jan-Jochem Randag, Koedijk (NL)

(73) Assignee: Dümmen Group B.V., De Lier (NL)

( * ) Notice: Subject to any disclaimer, the term of this patent is extended or adjusted under 35 U.S.C. 154(b) by 0 days.

(21) Appl. No.: 17/313,106

(22) Filed: May 6, 2021

(51) Int. Cl.
*A01H 5/02* (2018.01)
*A01H 6/10* (2018.01)

(52) U.S. Cl.
USPC ..... Plt./490
CPC ..... *A01H 6/10* (2018.05)

(58) Field of Classification Search
USPC ..... Plt./490
CPC ..... A01H 6/10
See application file for complete search history.

(56) References Cited

PUBLICATIONS

UPOV hit on Calla Lily plant named, 'Dozanatla', QZ PBR 20202100, filed Sep. 4, 2020.*

* cited by examiner

*Primary Examiner* — Anne Marie Grunberg
(74) *Attorney, Agent, or Firm* — The Webb Law Firm

(57) ABSTRACT

'Dozanatla' is a new variety of calla lily plant having dark purple colored spathes without a throat spot that produces 8-10 inflorescences per 16-18 cm tuber. The flower stems are about 21-27 cm in height. The leaves are dark to brownish green with maculations present and a smooth texture.

2 Drawing Sheets

Botanical classification: *Zantedeschia sprengeri*.
Varietal denomination: 'Dozanatla'.

BACKGROUND OF THE NEW PLANT

The present invention comprises a new and distinct variety of calla lily, botanically known as *Zantedeschia sprengeri* and hereinafter referred to by the varietal name 'Dozanatla'. 'Dozanatla' is a product of a planned breeding program, which had the objective of creating *Zantedeschia* hybrids for pot flower production in a wide range of colors with a classic flower shape. The new cultivar is a seedling selected from the crossing of *Zantedeschia sprengeri* seedling Z040918-701 (female parent, unpatented) with *Zantedeschia sprengeri* variety 'Allure' (male parent, unpatented). 'Dozanatla' was selected in 2009 by the inventor in 't Zand, The Netherlands as one flowering plant within the progeny of the stated cross.

The first act of asexual reproduction of 'Dozanatla' by tissue culture was performed by the inventor in January of 2012 in 't Zand, The Netherlands. Subsequent asexual reproductions by tissue culture at the same location have demonstrated that the combination of characteristics as herein disclosed for the new cultivar are retained and reproduced true to type through successive generations of asexual reproduction.

The following observations, measurements and comparisons describe plants at approximately 12 weeks from planting in 14 cm pots in 't Zand, The Netherlands under greenhouse conditions, which approximate those generally used in horticultural practice. Color references are made to The 2001 R.H.S. Colour Chart of The Royal Horticultural Society of London, $4^{th}$ Edition, except where general color terms of ordinary significance are used.

The present invention has not been evaluated under all possible environmental conditions. The phenotype may vary with variations in environment without a change in the genotype of the plant.

The following traits have been repeatedly observed and determined to be basic characteristics of 'Dozanatla' which, in combination, distinguish this calla lily as a new and distinct cultivar:

1. Medium purple colored spathes without a throat spot;
2. Dark to brownish green colored leaves; and
3. Few leaf maculations present.

The new variety is similar to its female parent in the following traits: lanceolate leaf shape, green stem color, and the presence of leaf maculations. However, 'Dozanatla' exhibits a narrower spathe width and shorter spathe length than its female parent. Further, its female parent has a red spathe color with a throat spot and a yellow/red spadix color. The new variety is similar to its male parent in the following traits: lanceolate leaf shape and the presence of leaf maculations. However, its male parent has a red spathe color with a throat spot and a yellow/red colored spadix.

When compared to calla lily plant named 'Purple Spirit' (U.S. Plant Pat. No. 29,648), both varieties exhibit dark colored spathes, but the upper and lower surface spathe colors of 'Purple Spirit' are from Red-Purple Group RHS 61A to 71A, while the upper surface spathe colors of 'Dozanatla' are from Greyed-Purple Group RHS N186B to N186C and the lower surface spathe colors of 'Dozanatla' are from Greyed-Purple Group RHS 187C to 187D.

BRIEF DESCRIPTION OF THE DRAWINGS

The accompanying photographic drawings illustrate the new variety taken at approximately 12 weeks of age, with the colors being as nearly true as is possible with color illustrations of this type.

DESCRIPTION OF THE NEW PLANT

Figure 1:
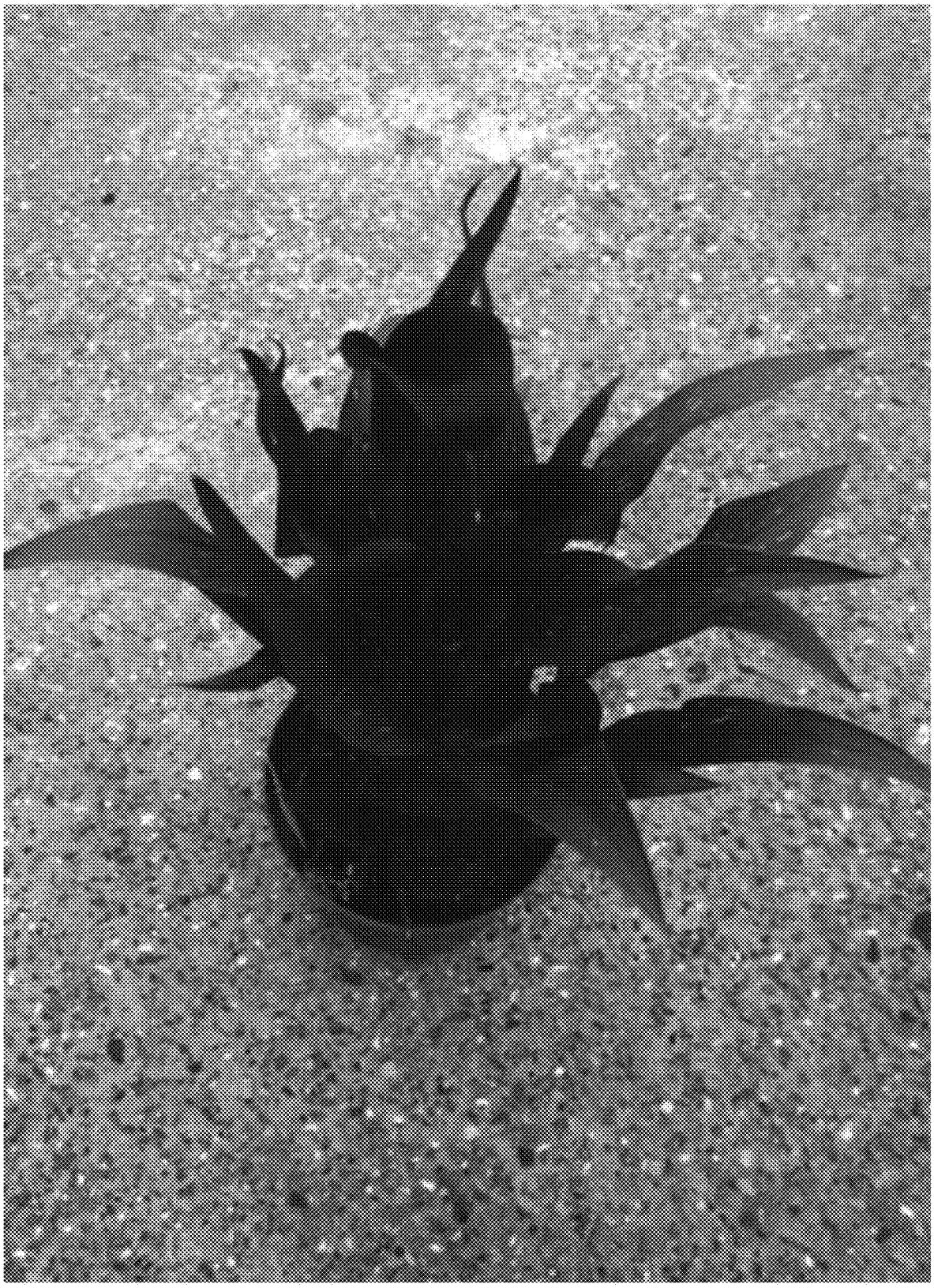
FIG. 1 illustrates a single flowering plant of the new variety.
Figure 2:
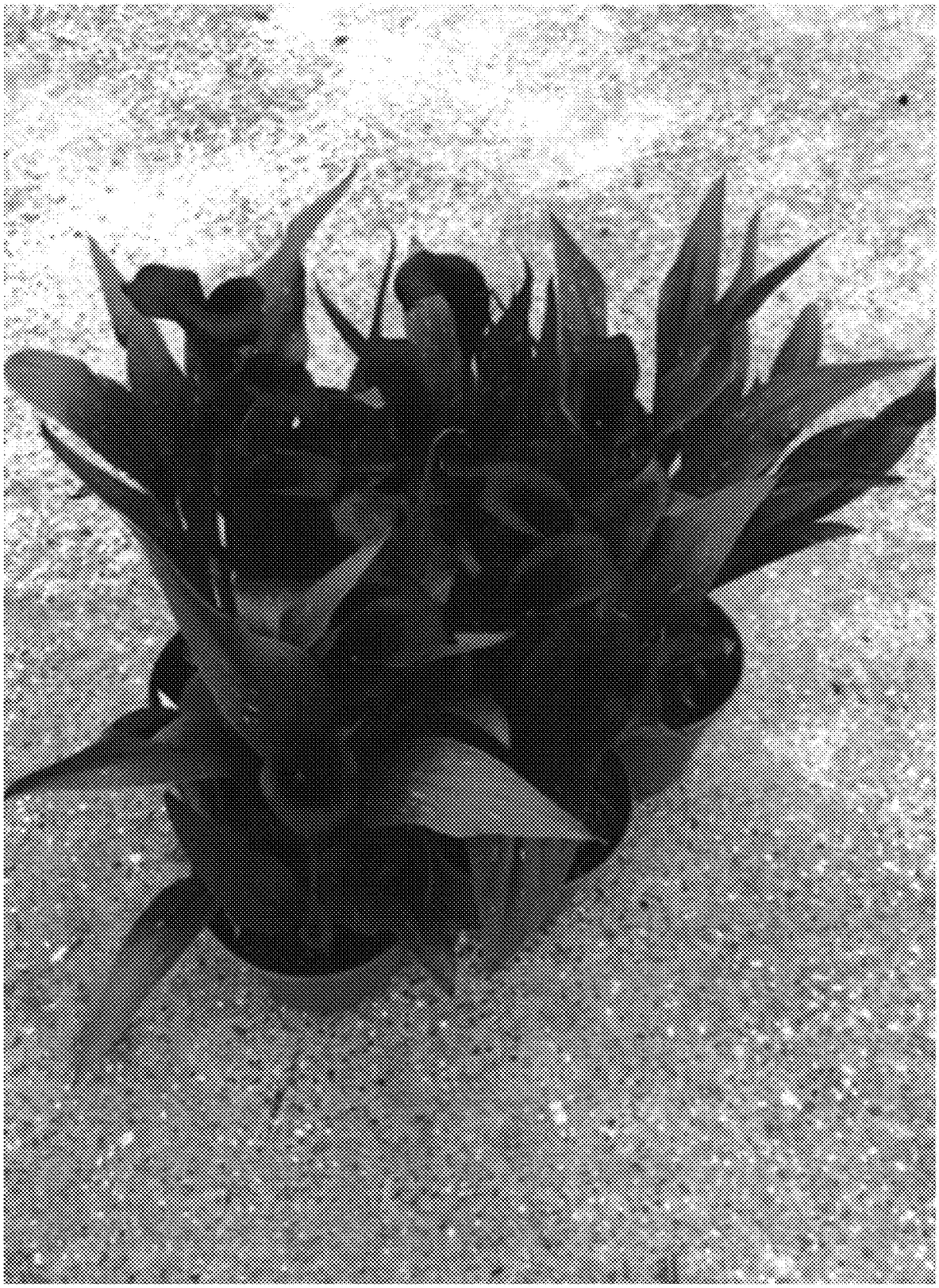
FIG. 2 illustrates multiple flowering plants of the new variety.

Type: Deciduous.

Size:

*Height of the leaf canopy above the soil.*—10-15 cm.

*Height of top of inflorescences above the soil.*—21-27 cm.

*Diameter.*—29-37 cm.

Form: Semi-spreading.

Number of inflorescences per tuber:

*Size* 16-18 *cm in diameter.*—8-10 inflorescences.

Branches:

*Number.*—Average.

*Color.*—Green Group RHS 138A to 138B.

*Young shoot color.*—Purple Group RHS N79B to N79C.

Leaves:

*Size.*—Width: 5-7 cm, with the broadest part being in the middle. Length: 18-23 cm.

*Number per plant.*—21-27.

*Leaf blade lobes.*—Absent.

*Shape.*—Lanceolate.

*Apex.*—Apiculate.

*Base.*—Attenuate.

*Margin.*—Entire; having a color of Green Group RHS 137A to 137B.

*Color.*—Upper surface: Green Group RHS 137A to 137B, with few, linear White Group RHS 155A to 155B maculations present. Lower surface: Green Group RHS 137D, with few, linear White Group RHS 155B maculations present.

*Veins.*—Configuration: Pinnate. Color: Green Group RHS 143A to 143B.

*Surface texture.*—Smooth (both surfaces).

*Petiole.*—Length: 11-15 cm. Diameter: 9-13 mm. Color: The base is Yellow-Green Group RHS 144C to 144D, the upper part is Green Group RHS 143B to 143C.

Roots:

*Color.*—White Group RHS 155C.

*Branching description.*—Fibrous root system. Several main roots emerge from the top of the tuber and form a small number of lateral roots.

Spathe:

*Size.*—Length (measured from opening to tip): 5.5-6 cm. Width: 4-4.5 cm. Height: 6-7 cm.

*Color.*—Throat spot: Absent. Upper surface: Greyed-Purple Group RHS N186B to N186C. Lower surface: Greyed-Purple Group RHS 187C to 187D.

*Vein color.*—Greyed-Purple Group RHS N186B to 186C.

*Shape.*—Leaf-like.

*Apex.*—Caudate.

*Base.*—Attenuate.

*Margin.*—Entire, with a color of Greyed-Purple Group RHS 187D.

Spadix:

*Shape.*—Cylinder.

*Size.*—Length: 25-35 mm. Diameter: 7-12 mm. Color: Greyed-Purple Group RHS 187B to 187C.

*Position relative to spathe.*—Upright.

Peduncle:

*Size.*—Length: 20-27 cm. Diameter: 7-10 mm.

*Color.*—The upper part is Yellow-Green Group RHS 146B to 146C, the lower part is Greyed-Green Group RHS 194A to 194B.

*Texture.*—Smooth.

Reproductive organs:

*Location of female organs.*—Basal position of the spadix.

*Location of male organs.*—Upper position of the spadix.

*Perianth.*—Conspicuous.

*Stamens.*—Presence: Not visible before pollen release. Number: Between 480 and 600. Pollen amount: Scarce. Color: Between White Group RHS 155B and 155C.

*Anther.*—Shape: Round. Length: Less than 1 mm. Color: Yellow Group RHS 8B to 8C.

*Filament.*—Length: Less than 1 mm. Color: White Group RHS 155D.

*Pistils.*—Number: 15 to 30. Length beyond perianth: About 1 mm.

*Stigma.*—Shape: Round. Size: Less than 1 mm.

*Style.*—Length: Less than 1 mm. Color: Yellow Group RHS 8B to 8C.

*Ovaries.*—Texture: Smooth. Length: Between 1 to 10 mm. Width: Between 1 to 10 mm. Color: The top color is Green Group RHS 139D, the bottom color is Greyed-Purple Group RHS 187A.

Seeds: None present.

Disease resistance: No unusual susceptibility/resistance to diseases noticed to date.

Pest resistance: No unusual susceptibility/resistance to pests noticed to date.

Heat tolerance: No heat tolerance.

Hardiness: Not tested to date.

Flowering: In general, the time from indoor and outdoor planting to first flowering takes about eight weeks in The Netherlands.

Lastingness: About two weeks on the plant.

Fragrance: None.

I claim:

1. A new and distinct variety of calla lily plant named 'Dozanatla' as herein described and illustrated.

* * * * *